(12) United States Patent
Pasquali (10) Patent No.: US 11,491,262 B2
(45) Date of Patent: Nov. 8, 2022

(54) METHOD OF BONE REGENERATION (71) Applicant: Paulo Jose Pasquali, Erechim (BR)

(72) Inventor: Paulo Jose Pasquali, Erechim (BR)

(73) Assignee: Paulo Jose Pasquali, Erechim (BR)

( * ) Notice: Subject to any disclaimer, the term of this patent is extended or adjusted under 35 U.S.C. 154(b) by 880 days.

(21) Appl. No.: 16/383,014

(22) Filed: Apr. 12, 2019

(65) Prior Publication Data

US 2019/0321517 A1    Oct. 24, 2019

Related U.S. Application Data

(60) Provisional application No. 62/659,776, filed on Apr. 19, 2018.

(51) Int. Cl.
*A61L 27/38* (2006.01)
*A61F 2/28* (2006.01)
*A61K 35/28* (2015.01)
*A61L 27/36* (2006.01)
*A61K 35/32* (2015.01)

(52) U.S. Cl.
CPC ............ *A61L 27/3821* (2013.01); *A61F 2/28* (2013.01); *A61K 35/28* (2013.01); *A61K 35/32* (2013.01); *A61L 27/3608* (2013.01); *A61L 27/3847* (2013.01); *A61L 2300/412* (2013.01)

(58) Field of Classification Search
CPC ......... A61F 2/2803; A61F 3/3099; A61C 8/00
See application file for complete search history.

(56) References Cited

U.S. PATENT DOCUMENTS

| | | | |
|---|---|---|---|
| 2004/0024457 A1* | 2/2004 | Boyce ...................... | A61F 2/08 623/13.17 |
| 2010/0215718 A1* | 8/2010 | Swords ................... | A61L 27/56 424/549 |
| 2011/0151400 A1* | 6/2011 | Boiangiu .............. | A61F 2/2803 433/76 |
| 2012/0207718 A1* | 8/2012 | Stone ...................... | A61P 19/00 623/14.12 |
| 2015/0050249 A1* | 2/2015 | Helms ................ | A61K 38/1709 435/366 |
| 2019/0117402 A1* | 4/2019 | Stevens ................... | A61L 27/56 |

* cited by examiner

*Primary Examiner* — Jason-Dennis N Stewart
(74) *Attorney, Agent, or Firm* — Jeffrey N. Townes; Cozen O'Connor (57) ABSTRACT

The present invention provides a method of bone regeneration for repairing a bone defect in a subject in need thereof. The method comprises the use of blood aspirate of the mandible bone marrow with the use of xenogen bone support.

19 Claims, 8 Drawing Sheets

| Name | Basal Bone | Graft | Total | |
|---|---|---|---|---|
| Patient 1 | 6,55 | 5,63 | 12,18 | 85 |
| Patient 2 | 5,85 | 4,55 | 10,40 | 77 |
| Patient 3 | 5,25 | 5,32 | 10,57 | 100,01 |
| Patient 4 | 4,60 | 5,00 | 9,60 | 100,08 |
| Patient 5 | 4,19 | 5,30 | 9,49 | 100,26 |
| Patient 6 | 3,87 | 4,61 | 8,48 | 100,19 |
| Patient 7 | 2,47 | 3,96 | 6,43 | 100,60 |
| Patient 8 | 2,45 | 5,51 | 7,96 | 100,24 |
| Patient 9 | 2,34 | 8,32 | 10,66 | 100,55 |
| Patient 10 | 1,48 | 4,98 | 6,46 | 100,36 |
| Patient 11 | 1,46 | 7,15 | 8,61 | 100,89 |
| Patient 12 | 1,05 | 4,67 | 5,72 | 100,41 |
| | | MEAN VOLUME OF THE GRAFT TOTAL = 5,41mm | | MEAN INCREASE IN GRAFT VOLUME TOTAL = 100,5% |

| Technique / Features | Technique of the present invention | Conventional techniques with xenograft |
|---|---|---|
| No. of professionals involved | 2 | 3 to 8 |
| Duration of the surgery | low | Medium to high |
| Cost | low | Medium to high |
| Patient recovery | Quick | Several days |
| Physical structure for the surgical intervention | Only dental structure | Dental and hospital structure |
| No. of surgical intervention | 1 | minimum of 2 |
| Contamination risk | low | Medium / high |
| Quality of obtaining bone tissue | Medium / high | low |
| Time necessary for performing the dental implants | 4 months | 6 to 8 months |

Figure 14

METHOD OF BONE REGENERATION

CROSS REFERENCE TO RELATED APPLICATIONS

This application hereby claims priority from U.S. Provisional Patent Application having Ser. No. 62/659,776 filed on Apr. 19, 2018, the contents of which are hereby incorporated by reference in their entirety.

FIELD OF THE INVENTION

The present invention refers generally to a method of regenerating bone. In particular, the invention refers to the use of aspirate of autologous bone marrow of mandibular origin, for bone tissue neoformation.

BACKGROUND

The preservation of life in its genetic tissue bases, are related to the principle of cellular reproduction, which seeks to maintain the homeostasis of cells, tissues, organs, systems as a whole, the balance and evolution of the human organism.

Cellular reproduction is supported by the principle of cell formation and differentiation, which is performed through the stem cells, both hematopoietic (HSCs) and mesenchymal (MSC) present in the bone marrow of various bones of the organism, wherein HSCs originates cells such as chondrocytes, adipocytes, among others, which have the ability to form the tissues of the organism.

The techniques currently being performed have the necessity of intervention in other areas of the patient body aiming to obtain bone marrow for tissue neoformation. These interventions for obtaining bone marrow, which are not effected in the oral area, cause trauma to the patient, often require more than one professional for this action—sometimes as many as eight professionals, prolong the duration of the surgery, and often require more than one surgical intervention. These techniques also inconvenience the patient more, as it requires at least two surgical interventions: one for obtaining the material to be grafted and another for grafting itself. As a result, the patients need several days for recovery, with 6 months typically needed for dental implants.

Moreover, treatments involving bone grafts often require protracted hospital stays which further increase the associated costs, burden the medical system, and represent an increased risk to the patient being treated.

Accordingly, a need exists for a technique that can be used to regenerate bone tissue in a reliable manner without undue risk of infection and without the need for prolonged and multiple surgical procedures and involving fewer professionals.

In addition, a safer, more efficacious and cost-effective method to promote bone regeneration, growth and repair with bone materials such as allografts and xenografts, is also needed.

Therefore, it is desired to overcome or reduce at least some of the above-described problems.

SUMMARY OF THE INVENTION

The present invention solves the problems of the art by providing a method of bone regeneration for repairing a bone defect in a subject in need thereof, wherein the method comprises the steps of:

Exposing the area of bone defect of the subject;
Fixing a graft in the receptor bed;
Aspirating the bone marrow blood from the mandible of the subject being treated;
Applying the collected mandibular bone marrow blood to the graft;
Placing a layer of barrier material over at least a portion of the graft.

In one embodiment of the invention, the bone defect is a lost or atrophied bone tissue.

In another embodiment of the invention, the bone repair site is an orthopaedic, periodontal, neurosurgical, oral or maxillofacial bone repair site.

In a preferred embodiment of the invention, the bone repair site is a periodontal bone repair site.

In one embodiment of the invention, the method further comprises placing a layer of barrier material over at least a portion of the graft.

In a preferred embodiment of the invention, the barrier is a non-absorbable biocompatible barrier.

In a more preferred embodiment, the barrier is a polypropylene barrier.

In one embodiment of the invention, the graft is a bone.

In a preferred embodiment of the invention, graft is of autogenous, allogenic or xenogeneic origin.

In a more preferred embodiment, the graft is of xenogeneic origin.

In one embodiment of the invention, the graft is obtained from porcine or bovine bone.

In one embodiment of the invention, the graft is in the form of block, particulate or assembly.

In one embodiment of the invention, the receptor bed is a remaining bone base.

In one embodiment of the invention, the subject is a mammal.

In a more preferred embodiment, the subject is human.

BRIEF DESCRIPTION OF THE DRAWINGS

FIG. 1.

DEFINITION

Unless defined otherwise, all technical and scientific terms used herein generally have the same meaning as commonly understood by one of ordinary skill in the art to which this invention belongs.

The term "autologous transplantation" or "autologous graft" refers to the removal of bone marrow blood from a patient itself, which may be of various bone origins (iliac crest, mandibular, tibia, skullcap, among others) where a specific kit is used and after blood collection is immediately inserted into the xenogeneic block which has been adapted previously to the remaining bone bases of the patient.

The terms "neoformation" and "regeneration" are interchangeably used herein.

The term "lyophilized" refers to the manner in which the product to be used is transformed; thus, its dehydration is performed where it becomes without presence of cells and proteins, thus avoiding possible immunological reactions. It is a product with only its inorganic structure, which in the case of innovation is used as a bone structure for MSC to differentiate and form the new bone tissue, replacing this lyophilized base.

The term used "homologous" it is reported that the punctured marrow blood originates from the same organism and that with the material the same objectives are sought.

The term "biocompatible" indicates the property that a natural or synthetic product does not produce immunological reactions to the patient.

The term "biodegradable" refers to the material used in bioregeneration which has the ability to perform its function and after a certain time is replaced or eliminated by the organism without leaving traces of interference in the grafting.

The term "mandibular bone marrow aspirate" indicates that the fluid (presence of mesenchymal cells) is aspirated from the mandibular bone marrow using the kit developed and cited and demonstrated by the innovation, or other suitable kits or techniques known in the art.

The term "barrier" refers to a sheet of suitable material, for example polypropylene material, used on grafting for the purpose of graft isolation.

The term "cell differentiation" is used when it is intended to relate what happens to the mesenchymal cells of the marrow to become specialized bone-forming cells (osteoblasts).

The term "bone defect" refers to a cavity in the bone structure, where there was partial or total loss of bone tissue. In one embodiment, puncture of the marrow blood of the mandible, which has differentiated presence of MSC, is inserted in this cavity with bone loss that will have a previously remodeled structure with xenogenous bone and this covered with this punctured material of the bone marrow, occurring after cell differentiation of MSC in osteoblasts, and these will form the new repair bone tissue. Then, on top of xenograft, a barrier is adapted for the purpose of tissue isolation.

The term "xenograft" refers to a 3D component, which may be from multi-origin (bovine, equine, among others), lyophilized, totally absent from the presence of cells, containing only inorganic materials in its structure, (marrow blood collected from the mandible) that will be added to it for stability of the transforming and regenerative process of the bone tissue. It is a biocompatible and biodegradable component that will be slowly replaced by new bone tissue formed. It can be made in different shapes, where they are sculpted beforehand by the professional and after being fixed in the remaining bone base and screwed. It can also be applied in the form of granules in bony structures that have cavities, following the same process mentioned above.

The term "MSC" is an abbreviation of mesenchymal stem cells.

The term "BMA" is an abbreviation of mandibular bone marrow blood.

The term "osteogenic" refers to cells capable of forming bone tissue.

DETAILED DESCRIPTION OF THE INVENTION

This invention is not limited in its application to the details of construction and the arrangement of components set forth in the following description or illustrated in the drawings. The invention is capable of other embodiments and of being practiced or of being carried out in various ways.

Also, the phraseology and terminology used herein is for the purpose of description and should not be regarded as limiting.

The present invention refers to a method of bone regeneration, using the mandibular bone marrow (MBM), for being a source rich in mesenchymal stem cells, wherein they are used as a base rich in regenerative potential. Its achievement is carried out in a protocolized and specific manner in each region of the body that will be obtained, always following the principles of cellular preservation, maintaining the medium of cellular reproduction balanced, and the least possible trauma to the patient being rehabilitated.

Mandibular marrow may be obtained by a protocol properly developed, following the standards of the Regulatory Agencies of these interventions. The technique of obtaining bone marrow of mandibular origin seeks a lower trauma to the patient and greater facility of obtaining MSC, without having the necessity of intervention in other regions that are not of the area of dental performance, with the intention of bone tissue neoformation, through of differentiation of MSC into osteoblasts (bone tissue-forming cells).

The present invention uses the principles of guided-tissue regeneration, where a quantity of aspirate necessary for a specific bone graft is removed from specific region(s) of the mandible. The bone graft will be a neoformed bone base for the installation of dental implants with the functional stomatognathic rehabilitation.

Particularly, the aspiration can be effected in any region of the mandible. The quantity of mandibular aspirate necessary for the bone graft is determined in each case, depending on the patient conditions and is related to the quantity to be grafted.

The invention also provides the uses lyophilized structures of bone tissue of diverse origins (bovine, equine, among others) for the architectural maintenance of the process of neoformations above xenograft, where a polypropylene barrier may be used to separate the grafted tissue. The barrier remains in the grafted medium the time necessary for tissue identification, after the specific timeframe, the barrier can be removed or not, depending on the site where the grafting was performed.

The need for removal and the time in which the barrier is maintained in the grafted medium is determined for each case, which will be dependent on the patient's condition, the size of the graft and the complexity of the surgical intervention, and other factors known to one skilled in the art. Typically, the barrier is maintained for at least 30 days in the patient.

Figure 1:
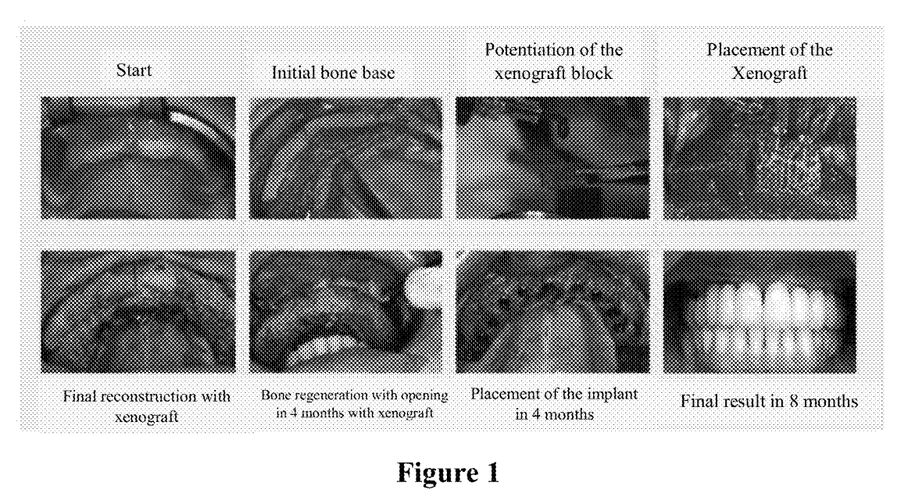
FIG. 1 is a series of images depicting an example of the steps of the method for bone regeneration for a periodontal bone repair site.
Figure 2:
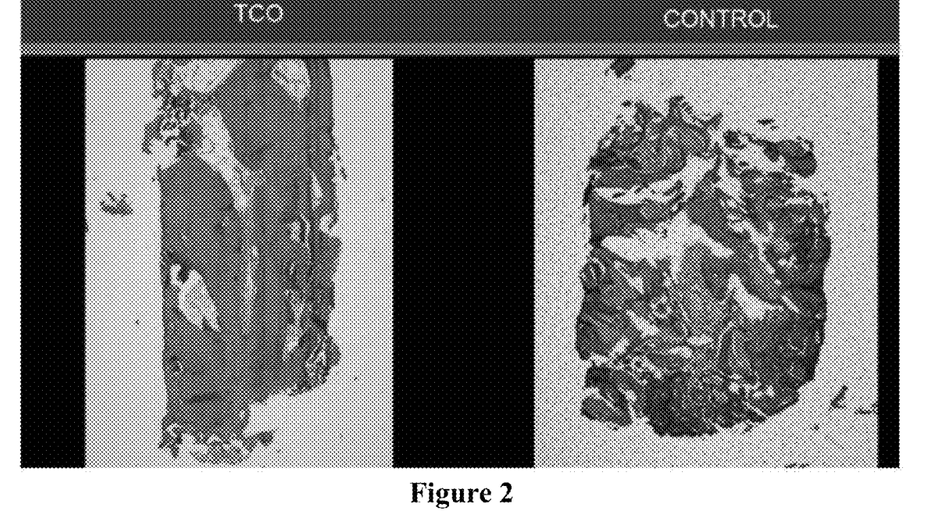
FIG. 2: View of histological sections showing vital bone formation comparing the present technique (TCO) with conventional techniques (Control).
Figure 3:
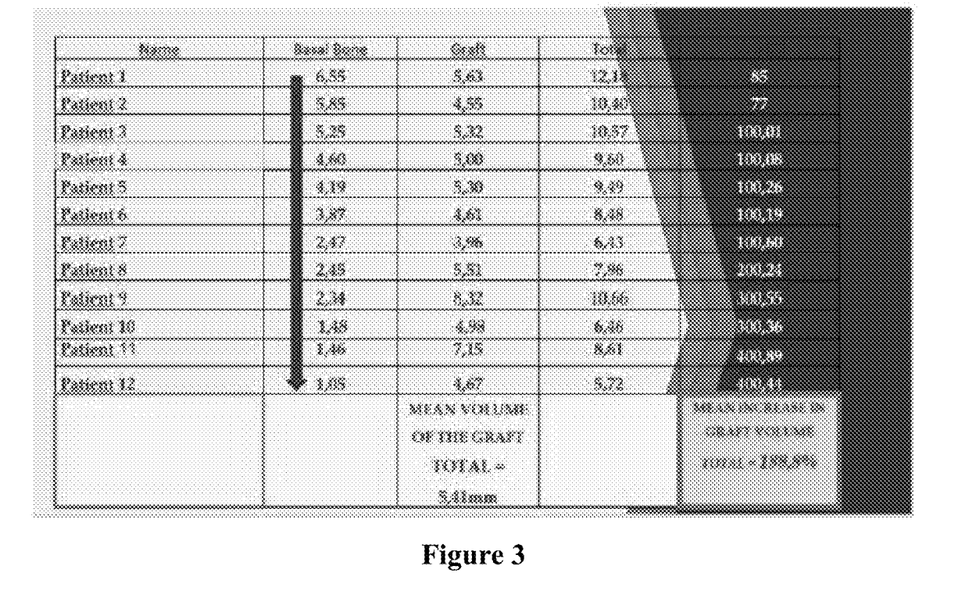
FIG. 3: Table showing the average percentage of increase in the total volume of grafting, the potential of the technique in use in critical areas of loss of bone structure, the developed and evaluated clinically/laboratorially, proving the innovation potential when performing xenogeneic grafts in critical bone bases, the percentage increase of volumetric formation of the xenograft technique.
Figure 4:
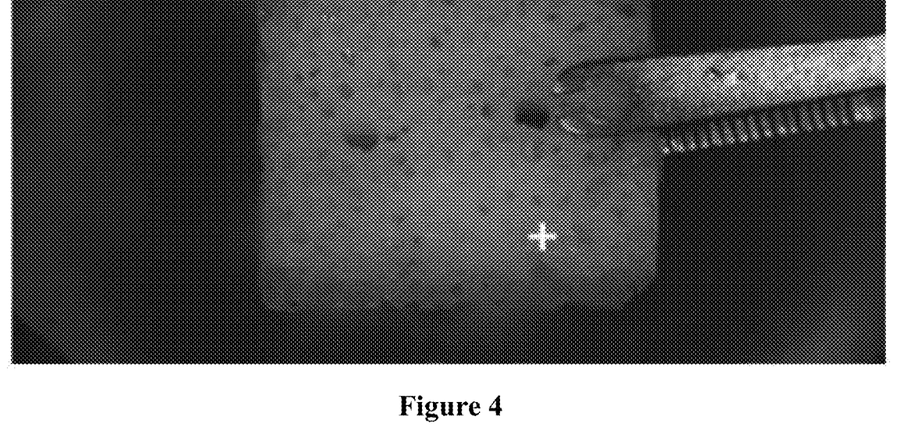
FIG. 4: 3D view of a xenograft bone that may be used in the disclosed techniques.
Figure 5:
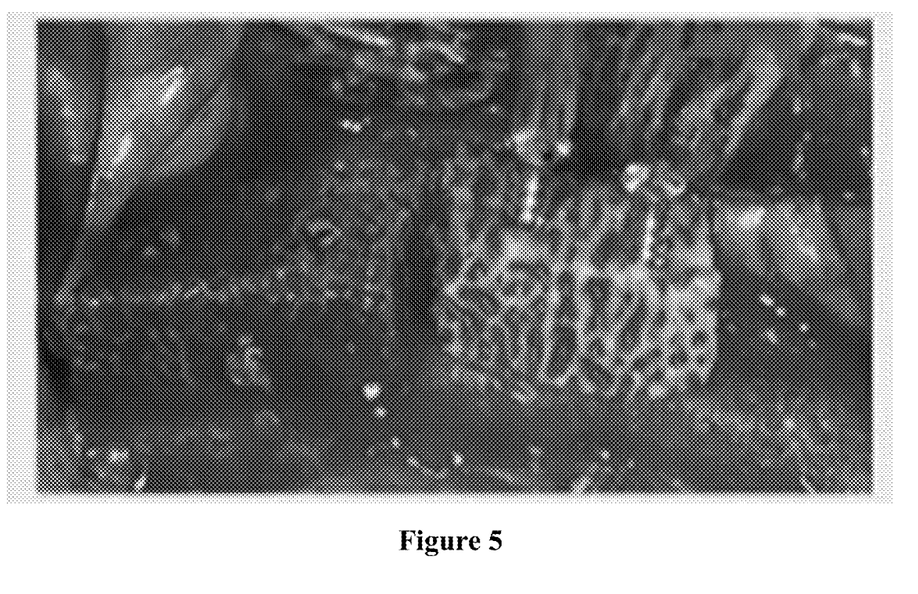
FIG. 5: View of the fixation of the xenograft block.
Figure 6:
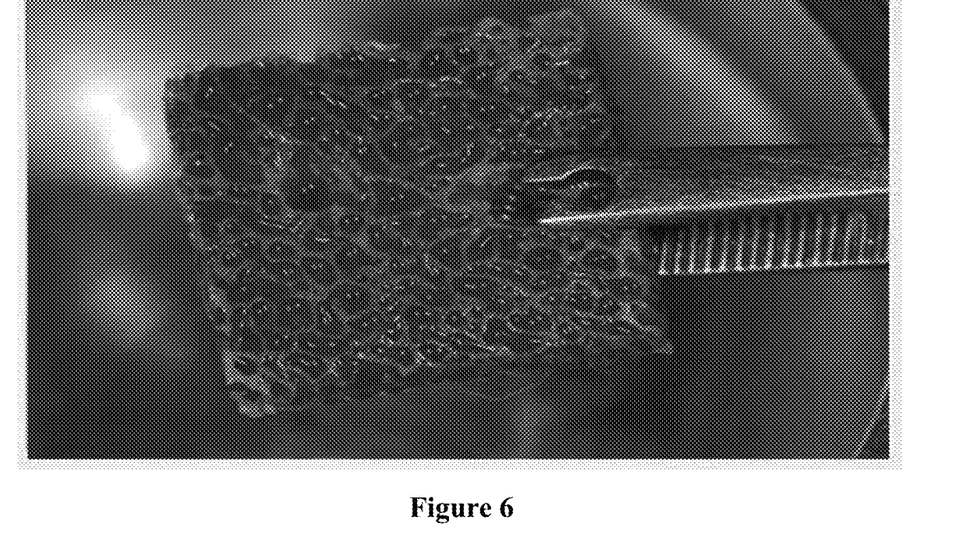
FIG. 6: View of xenograft block humidified with marrow blood.
Figure 7:
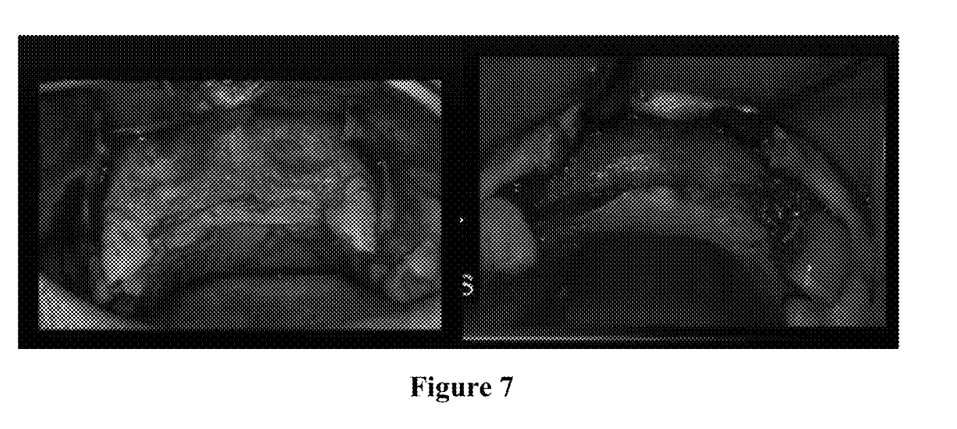
FIG. 7: View of the initial and final bone regeneration process.
Figure 8:
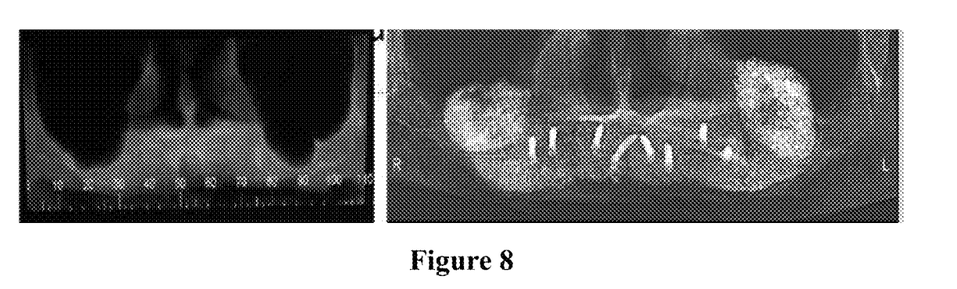
FIG. 8: Tomographic view of the process of bone neoformation performed by the present invention.
Figure 9:
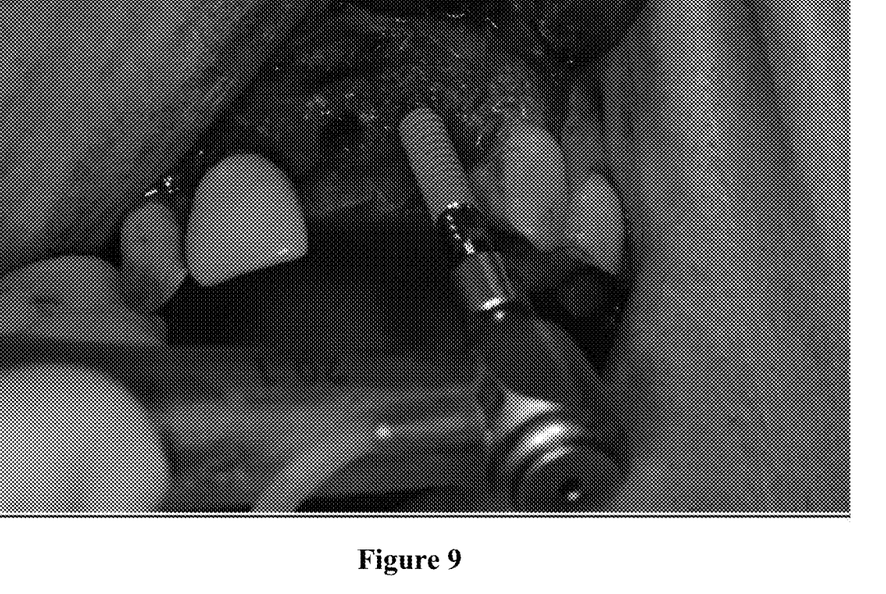
FIG. 9: View of the insertion of the implant(s) into the new bone neoformed by the method of the invention.
Figure 10:
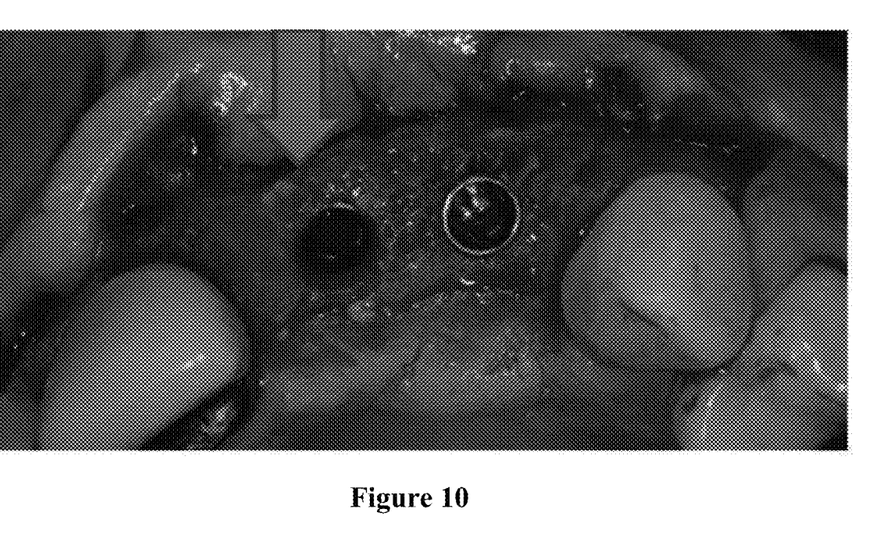
FIG. 10: View of the bone contour restored by the method of the invention.
Figure 11:
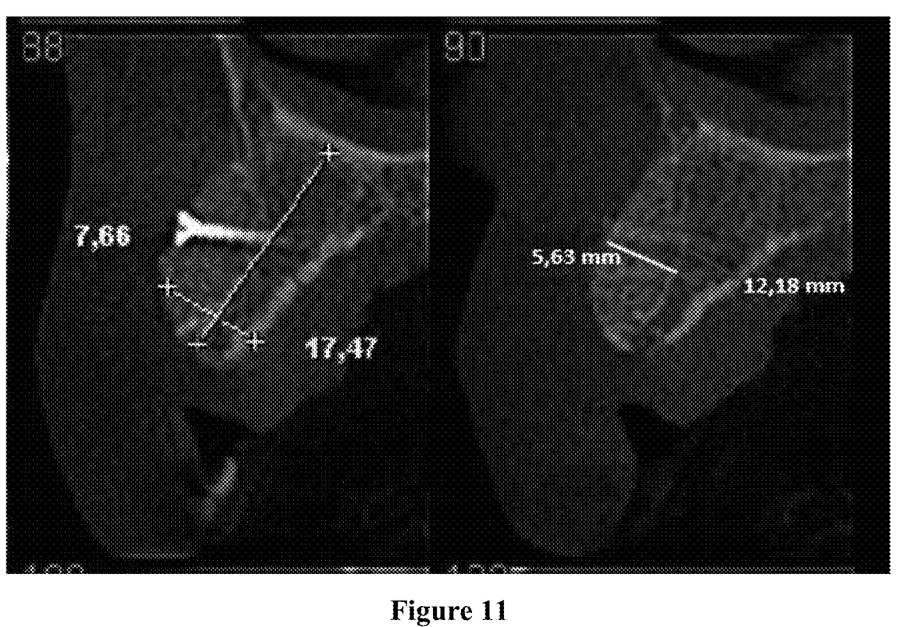
FIG. 11: View of tomographic sections demonstrating bone formation and consolidation obtained by the present method.
Figure 12:
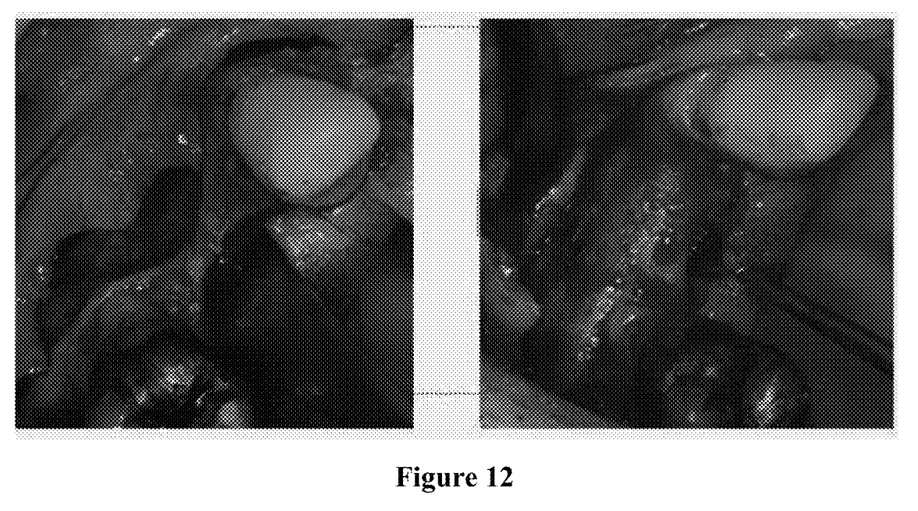
FIG. 12: View of before and after of the xenogeneic graft in a critical zone of the remaining base area.
Figure 13:
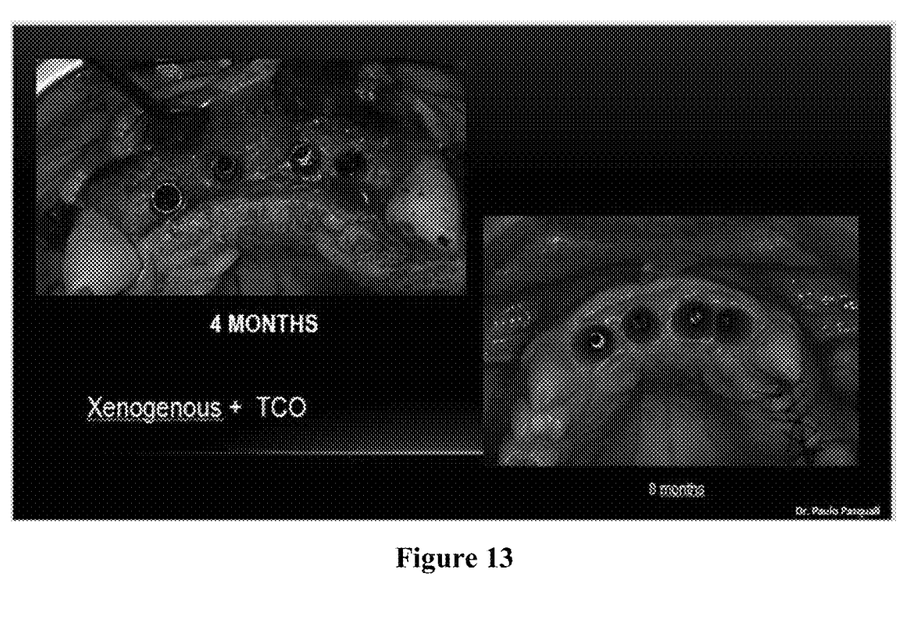
FIG. 13: View showing the regenerative and rehabilitating capacity of the method of the invention, through the 4-month clinical aspect (implant installation) and 8 months (prosthetic rehabilitation).
Figure 14:
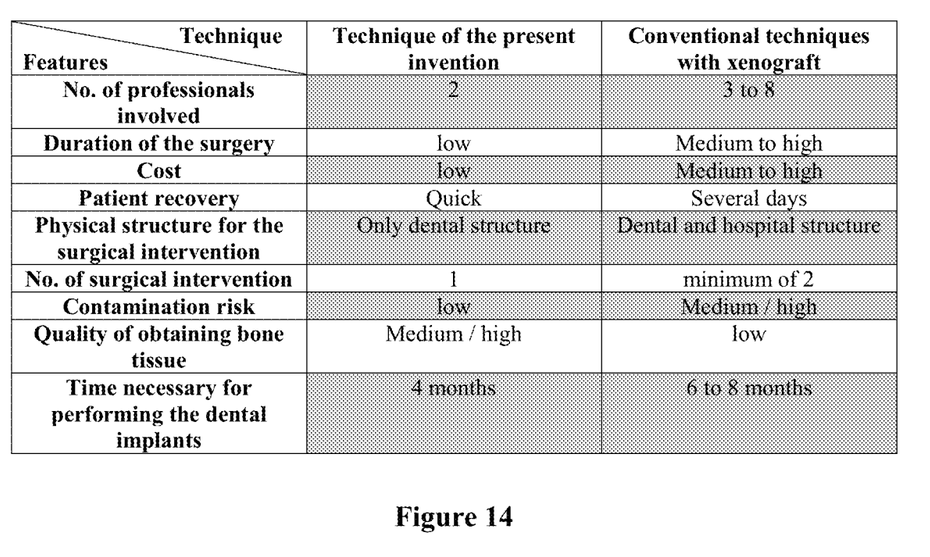
FIG. 14: Table showing a comparison between certain aspects of the conventional technique known in the art and certain aspects of the technique of the present invention.

The technique generally relates to reconstruction of lost tissue/bone structures in a simple and practical manner, where only one (1) professional with an auxiliary professional can perform the collection and grafting in a single session. It is a technique that potentiates the grafts, since, it seeks the cells that differentiate into specific bone tissue-forming cells (bone, cartilage, among others) in a different location from the grafted site. It is an effective technique because it causes less trauma to the patient and with fewer professionals involved, reducing costs, and with results above the traditional results obtained by performing bone marrow puncture of the iliac bone or not. The comparison of the certain aspects of the traditional technique compared with certain aspects the technique of the present invention is provided in FIG. 14.

The present technique is an increment to the bone grafting process, because, when removing mandibular marrow blood and reimplanting in the same patient, being known as an autologous process, in a place with lower concentration of MSC, it will develop in the grafted site, wherein the graft is a xenograft, biocompatible and biodegradable graft, a larger ability of cell differentiation, resulting in a higher quality and quantity of vital mineralized bone tissue.

In one embodiment, the present method provides an autologous technique, in which it is totally free of any immunological adverse reactions.

The procedure also has the capacity to potentiate xenografts/allografts from both the implant and orthopedic areas and has the potential to add cellularity in tissue engineering of acellular biomaterials.

The present invention also, in one embodiment, comprises a step of incorporating a polypropylene barrier, which has the purpose of separating the soft and hard tissues, thus avoiding a tissue mixture, and a lower quality and quantity of undesired neoformed tissue. Another embodiment relates to the use of kit for marrow puncture, which assists in the collection of the mandibular marrow of the patient.

The present invention also provides a capacity to reconstitute the bony bases of the face, aiding in the harmonization/re-harmonization of the tissues that compose the human face.

In some embodiments, the invention is an autotransplantation or autologous process, in which it does not have the capacity to generate immunological reactions.

The present invention also provides the ability to increase soft tissue formation by having in its technique a higher concentration of MSC than the traditional concentrations of peripheral blood circulating in the tissues of the human body. The present invention comprises the step of using the bone marrow from the mandible to form bone tissue. In one embodiment, the present invention provides differentiation of adult mesenchymal cells into bone-forming cells (osteoblasts), and consequently, greater differentiation and formation of bone-forming cells (osteoblasts), occurring an increase in the graft that will be used of the mandibular bone marrow, obtaining, therefore, a greater bone quality in a short time, compared to the conventional techniques. The present invention provides, in alternative embodiments, a method of bone regeneration, comprising the steps of:

Carrying out an anamnesis of the patient and the appropriate complementary tomographic and laboratory exams, with the objective of protection and safety for the patient, the appointment is scheduled to perform the surgical act itself.

Performing the antisepsis of the patient.

Performing the infiltrative anesthesia at the site where the grafting with graft material will be effected.

In a particular embodiment, the graft material is of xenogenic, allogenic or autogenic origin.

In a more particular embodiment, the graft material is a xenogenic graft.

In another embodiment of the invention, the graft is a block, a particulate or in conjunction.

Exposing the bone defect may involve performing the gingival distance (divulsion) of the area that will receive the graft, which may follow, for instance, the decorticalization of the cortical bone wall with carbite steel spherical drill.

In the case of a block xenogenic graft, the grafting is sculpt in order to better adapt it to the receptor bed. In the case of a particulate graft, the particles are accommodated at the site to be grafted.

In the case of association of the block and particulate grafts, the particle bone is used around the block so that a better adaptation of the entire grafting process occurs.

When using blocks, they are screwed into the bone base to be grafted, with, for example, screws specific for dental bone grafting, which have different sizes and thicknesses, being chosen according to the extension and size of the grafting to be performed, if necessary, is adapted peripherally to the xenogene block, xenogenous particulate bone.

If the grafting at the maxillary sinus(es) is needed, the method comprises the steps of opening the external wall of the maxillary sinus to be grafted, lifting the peri-sinusal inner membrane, and then the effecting the insertion of the xenogeneous particulate bone into the sinus cavity.

After the preparation of the graft in the receptor bed is completed, the mandibular marrow blood is collected, with, for example, the following steps:

Choosing the site of collection of the marrow, using, for instance, tomographic analysis, which provides information for deciding the easier site for collection, as well as the site of lower risk for the patient.

Performing the local infiltrative anesthesia, if needed, and subsequently exposing the bone tissue, for instance the cortical bone tissue, with, for example, an incision around 1 centimeter. The access to the marrow may be performed by using a drill. Thereafter, the marrow blood puncture may be performed. All material used for proper puncture may be covered with heparin.

The collection of the marrow may occur by, for example, traction of the plunger of the syringe, collecting the marrow material in amount previously calculated by the dental surgeon.

Once the collection is completed, blood hemostasis is expected, which can be done by, for instance, simple compression at the site that has been punctured with a sterile gauze, and then sutured the gingival tissue that has been removed.

After collection, this marrow can be immediately applied to the graft material grafted into the remaining bone base, making the graft material fully embedded with this bone marrow. In the case of graft in the maxillary sinus, the bone marrow after being collected may be inserted into the maxillary sinus previously placed the bone. Afterwards, in both cases, the graft may be covered with a barrier to improve the bioactivity of the bone formation.

The barrier may be non-absorbable biocompatible, which may require the need to be removed at the right time, as defined by the surgeon according to the graft and type of grafting being performed. When the removal of the barrier is desired, an incision of approximately 0.5 cm can be made in the tissue covering the barrier and this barrier will be exposed, and with, for instance, a sterilized clinical clamp the barrier will be drawn and removed, and a suture will be performed on the tissue that was covering the barrier. In case of block xenogen graft, this graft may also be covered by this type of barrier, following the same steps according to the grafting that is being performed.

In the case of grafts in xenogen block, in order to reconstitute bone loss of the jaw, this process of bone neoformation will typically occur, on average, around 4 months. After this period, in case of dental implants, the screws fixation of blocks are removed, and this bone neoformation will typically occur around 6 months in the maxillary sinuses. Therefore, the method of the present invention provides an increased bone neoformation, to restore facial bone deformities, without the need to remove autogenous bone tissue from the patient. This is because, often times, when autogenous bone is removed, it is known of complexity, morbidity, difficulty of recovery, and there is a need for more professionals to participate in the surgical procedure. This can be eliminated with the technique described above, since, besides being a predictable technique, it also does not have autogenous graft morbidities, requiring only 2 professionals to perform it.

EXAMPLE

Case Study

After performing the basic procedures necessary for a surgical intervention for grafting, the steps of the technique follow the following order:

Initially, local anesthesia and gingival clearance was performed on the site to be grafted. Subsequently, the graft receptor bone bed was prepared, with proper decorticalization (microperforations in the basal bone). In the sequence, the xenogen block is sculpted if it is to be used, or only the particulate xenogenous bone, or both together. The xenogenic blocks are fixed with specific screws for grafting, and if necessary the peripheral adaptations of the block with particulate xenogenous bone are finished. Thereafter, the marrow blood was obtained as described above, and this was inserted into the xenogenic block (s) adapted to the surgical bed. After that, a polypropylene barrier covering the grafted material was adapted. A conventional suture is performed, at the discretion of the surgeon, and the barrier was removed in due time according as the graft is objectified.

The foregoing detailed description has been given for clearness of understanding only, and no unnecessary limitations should be understood therefrom, as modifications will be obvious to those skilled in the art.

I claim:

1. A method of bone regeneration for repairing a bone defect in a subject in need thereof, wherein the method comprises the steps of:
    exposing a bone repair site in the subject, wherein the bone repair site contains a bone having a bone defect;
    fixing a graft containing bone-tissue-forming cells in the receptor bed of the bone;
    performing a marrow blood marrow puncture to collect bone marrow blood and covering the blood marrow puncture with heparin;
    collecting bone marrow blood from the mandible of the subject being treated;
    applying the collected mandibular bone marrow blood to the graft; and
    placing a layer of barrier material over at least a portion of the graft.
2. The method according to claim 1, wherein the bone defect is a lost or atrophied bone tissue.
3. The method according to claim 1, wherein the bone repair site is an orthopedic, periodontal, neurosurgical, oral or maxillofacial bone repair site.
4. The method according to claim 3, wherein the bone repair site is a periodontal bone repair site.
5. The method according to claim 1, wherein the barrier is a non-absorbable biocompatible barrier.
6. The method according to claim 5, wherein the barrier is a polypropylene barrier.
7. The method according to claim 1, wherein the graft is a bone graft.
8. The method according to claim 7, wherein the bone graft is of autogenous, allogenic or xenogeneic origin.
9. The method according to claim 8, wherein the bone graft is of xenogeneic origin.
10. The method according to claim 9, wherein the bone graft is obtained from porcine or bovine bone.
11. The method according to claim 1, wherein the graft is in the form of a block, particulate or assembly.
12. The method according to claim 1, wherein the receptor bed is the remaining bone base in the bone.
13. The method according to claim 1, wherein the subject is a mammal.
14. The method according to claim 13, wherein the subject is human.
15. The method according to claim 1, wherein the exposing step comprises treating the bone repair site with local anesthesia and/or providing gingival clearance.
16. The method according to claim 1, wherein the collecting step comprises aspirating the bone marrow blood from the mandible.
17. The method according to claim 1, wherein the applying step comprises humidifying the graft with the bone marrow blood.
18. The method according to claim 1, wherein the graft is a block graft and wherein the block is a surgical implant.
19. The method according to claim 18, wherein the implant is a dental implant.

* * * * *